(12) United States Patent
Lennon

(10) Patent No.: US 6,503,199 B1
(45) Date of Patent: Jan. 7, 2003

(54) UNIFORM VOLUMETRIC SCANNING ULTRASONIC DIAGNOSTIC IMAGING SYSTEM

(75) Inventor: Daniel Lennon, Clinton, WA (US)

(73) Assignee: ATL Ultrasound, Bothell, WA (US)

( * ) Notice: Subject to any disclaimer, the term of this patent is extended or adjusted under 35 U.S.C. 154(b) by 0 days.

(21) Appl. No.: 09/433,124

(22) Filed: Nov. 3, 1999

(51) Int. Cl.$^7$ .................................................. A61B 8/00
(52) U.S. Cl. ...................... 600/443; 128/916; 600/447
(58) Field of Search ................. 600/443, 447; 128/916

(56) References Cited

U.S. PATENT DOCUMENTS

| | | | |
|---|---|---|---|
| 4,310,907 A | | 1/1982 | Tachita et al. |
| 4,582,065 A | * | 4/1986 | Adams ........................ 600/447 |
| 5,159,931 A | * | 11/1992 | Pini ............................ 600/443 |
| 5,181,514 A | | 1/1993 | Solomon et al. |
| 5,797,846 A | * | 8/1998 | Seyed-Bolorforosh et al. .. 600/447 |
| 5,846,200 A | | 12/1998 | Schwartz |
| 5,865,750 A | * | 2/1999 | Hatfield et al. .............. 128/916 |
| 5,967,985 A | * | 10/1999 | Hayakawa ................... 600/447 |

OTHER PUBLICATIONS

McCann et al., "Multidimensional Ultrasonic Imaging for Cardiology," pp. 1063–1073, Proceedings of the IEEE, vol. 76, No. 9, Sep. 1988.

* cited by examiner

*Primary Examiner*—Francis J. Jaworski
(74) *Attorney, Agent, or Firm*—W. Brinton Yorks, Jr.

(57) ABSTRACT

An ultrasonic diagnostic imaging system and method are described for more uniformly scanning a volumetric region for 3D ultrasonic imaging. An image plane of steered scanning beams is rotated about an axis extending through the volumetric region with beams in the vicinity of the axis more widely separated than beams more remotely located from the axis. The nonuniform spacing of the scanning beams results in relatively less disparate sampling densities across the scanned volumetric region. The inventive method may be performed with both 1D and 2D array transducers.

15 Claims, 2 Drawing Sheets

UNIFORM VOLUMETRIC SCANNING ULTRASONIC DIAGNOSTIC IMAGING SYSTEM

This invention relates to ultrasonic diagnostic imaging systems and, in particular, to ultrasonic diagnostic imaging systems which uniformly scan a volumetric region for three dimensional imaging.

When a volumetric region or three dimensional object is ultrasonically scanned for three dimensional imaging, it is desirable to completely and adequately sample or scan the region or object so that the resultant three dimensional image faithfully and completely represents the volumetric or three dimensional object. A number of techniques have been proposed for ultrasonically scanning volumetric regions with the array transducer scanheads widely in use today for conventional two dimensional planar imaging. Since array scanheads operate by scanning an image plane, an image volume may be scanned by sweeping the scanhead's image plane through the volumetric region of interest. U.S. Pat. Nos. 5,353,354 and 5,474,073 describe a linear sweep technique by which a sequence of parallel image planes are acquired as the scanhead is moved across the volumetric region and the image plane moves through the region being scanned. The acquired image data has the x and y coordinates of the scanhead's image plane, and each spatially distinct plane defines a z coordinate. When the scanhead produces a sector scan, the volume swept will have a wedge shape. When the scanhead produces a linear scan of parallel scanlines in each plane, the volume swept will have a cubic or rectangular box shape.

A second volumetric scanning technique is to rock or fan the scanhead about a pivot point at the skin surface. A device which precisely produces this rocking motion is described in U.S. Pat. No. 5,487,388. Depending upon the shape of the two dimensional image plane of the scanhead (linear or sector), this fanning technique will sweep through a wedge or pyramidal shaped volume of the body.

Yet a third volumetric scanning technique is to rotate the scanhead about a pivot point. This technique will sweep through a cylindrical or conical volume of the body when the scanhead is rotated about the center of the image plane, depending upon whether the scan plane is linear or sector shaped. Both external and internally operating scanheads have been developed for performing this scanning. The article "Multidimensional Ultrasonic Imaging for Cardiology" by McCann et al., published in the Proceedings of the IEEE, vol. 76, no. 9 (September 1988) at pages 1063–73 illustrates the rotational scan plane technique and describes an externally applied scanhead which scans the heart transthoracically. The scan plane is rotated by rotating a phased array transducer in angular increments with a stepper motor. The use of the motor enables uniform control of the angular increments; in an illustrated application the scan plane is stepped in increments of exactly 1.8°. The rotational volumetric scanning technique can also be performed internal to the body with a multiplane transesophageal echocardiography (TEE) probe as described in U.S. Pat. No. 5,181,514. Since a multiplane TEE probe inherently performs the function of rotating an array transducer about its center, successive scan planes can be acquired and stored as the array transducer is rotated and used to form a three dimensional image.

The McCann et al. article refers to a characteristic of rotationally acquired image data, which is the nonuniform distribution of the image data. The data density is relatively high around the axis of rotation and relatively low at the periphery of the scanned volume. McCann et al. deal with this nonuniformity by filling in the spaces between pixels at the periphery by hole filling, a process also referred to as interpolation, filtering or smoothing. As McCann et al. point out, this processing can be intensive: up to ten iterations of smoothing were required by McCann et al. to produce a pleasing image. Unmentioned by McCann et al. is the possibility that the periphery may be spatially undersampled, leading to artifacts and inaccuracies in the smoothed data. It would be desirable to reduce or eliminate this problem with a scanning technique that produced more homogeneous, uniformly sampled volumetric data.

In accordance with the principles of the present invention, a technique and apparatus are provided for uniformly scanning a volumetric region about a central axis. Scanning beams in proximity to the central axis are relatively widely separated while satisfying the desired criteria for spatial sampling density. Toward the periphery of the volume the scanning beams are relatively more closely spaced to better equalize the spatial sampling densities at the central and peripheral locations of the volumetric region. A scanhead for performing the inventive technique is described having an array transducer which transmits and receives beams that are more widely spaced toward the center of the array and more closely spaced toward the ends of the array. Mechanical or electronic rotation of the array produces more uniformly sampled volumetric image data.

Figure 1:
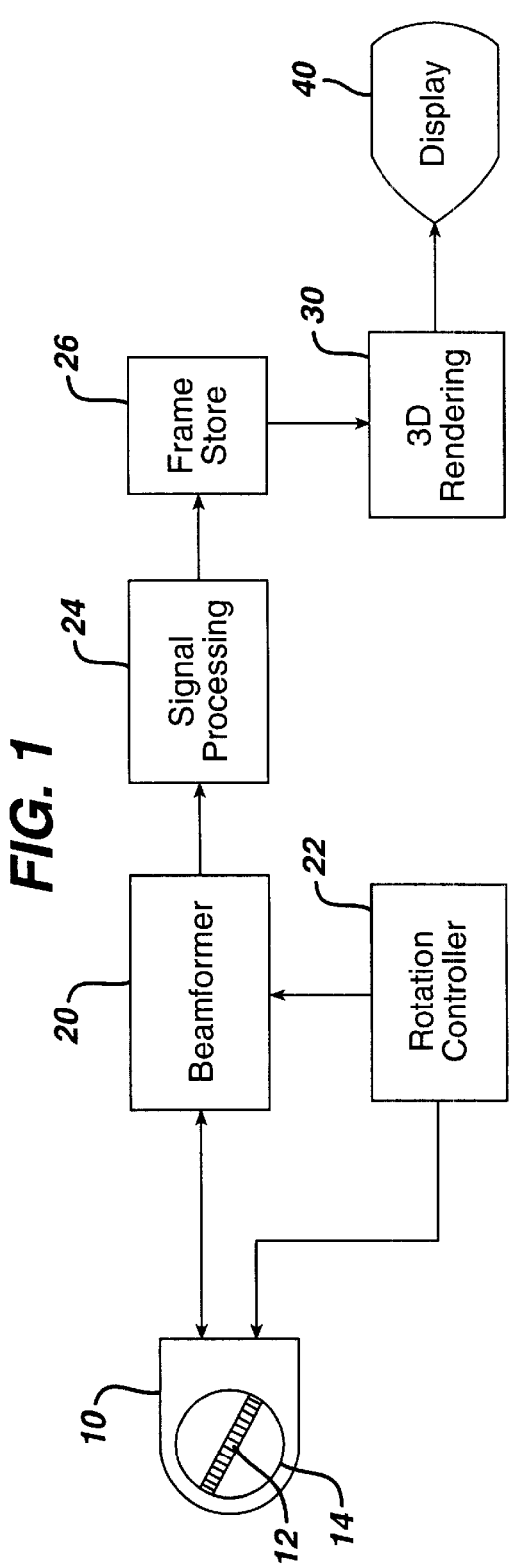
FIG. 1 illustrates in block diagram form an ultrasonic diagnostic imaging system and scanhead constructed in accordance with the principles of the present invention.

Referring first to FIG. 1, an ultrasonic diagnostic imaging system and scanhead constructed in accordance with the principles of the present invention are shown. The scanhead 10 includes a housing in which a rotating transducer array 12 is located. The transducer array 12 is rotated in a circular aperture 14. The illustrated array 12 is a 1D array which can only steer beams in the azimuth direction of a scan plane. Such a transducer array is mechanically rotated by a motor in the housing, under control of a rotation controller 22. The motor may be a linear or stepper motor of a multiplane TEE probe as described in U.S. Pat. No. 5,402,793, or the motor of a trans-thoracic rotating array probe such as that described by McCann et al. As the motor rotates the 1D array transducer, its scan plane is rotated about the axis of rotation. Preferably the axis of rotation passes through the center of the array, that is, the array transducer is rotated about its center, but embodiments in which the array transducer is rotated about an off-center axis are also suitable. When the array transducer is a 2D array, beams can be electronically steered in both azimuth and elevation. In such case it is not necessary to mechanically rotate the transducer. The beams can be steered electronically in both elevation and azimuth about a central axis of the volumetric region by control of the steering delays of the transmit and receive beamformers.

The scanhead 10 is coupled to a beamformer 20 which controls the transmit steering and focusing of the beams produced by the array transducer 12, and the steering and dynamic focusing of received beams. The scanhead 10 is also coupled to the rotation controller 22 as described above. When the rotation controller 22 performs mechanical rotation of the array transducer, rotational information is provided to the beamformer 20 so that the transmission and reception of beams is coordinated with rotation of the transducer. The rotational information may be provided by a shaft encoder or counter, for example, which track rotation of the transducer array. In an embodiment which electronically steers 2D array beams, the rotation controller need not be coupled to the scanhead, but can be used to provide steering delay information for a desired sequence of steered beams to the beamformer 20. In either case, the beamformer controls the array transducer to scan a volumetric region of the body with ultrasonic beams.

The coherent receive beams formed by the beamformer 20 are coupled to signal processing circuitry 24. The signal processing circuitry operates as is known in the art to produce ultrasonic image signals of tissue, motion or flow. The signal processing circuitry can process fundamental or harmonic signals for detection and processing as grayscale or Doppler image signals, for instance. Filtering and compounding of the ultrasound signals may also be performed by the signal processing circuitry. The image signals are then stored in a frame store 26 in correspondence to their locations in a volumetric data array or a series of planar data arrays. The frame store may also include scan conversion functions to further process or orient the image signals into a desired display format with polar or rectilinear coordinates.

The image signals acquired from a volumetric region of the body are coupled to a 3D rendering processor 30. The 3D rendering processor may use any type of known processing to form a 3D image presentation. The 3D rendering processor may process the volumetric data to form a surface rendering, which is useful for 3D imaging of the face of a fetus or the wall or surface of an organ such as the heart. The 3D rendering processor may also perform volumetric rendering, which is useful to form a 3D image of vascular flow such as the coronary or renal arteries. In any case, the 3D display signals produced by the 3D rendering processor are coupled to a display device 40 which is capable of displaying the desired three dimensional ultrasonic image.

Figure 2:
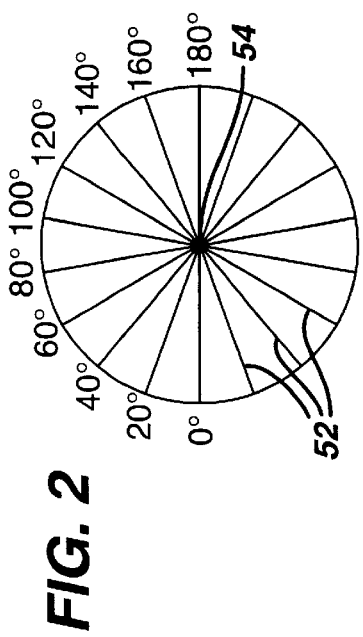
FIG. 2 illustrates volumetric scanning by rotation of a scan plane.

FIG. 2 is a top view of a cylindrical volumetric region 50 which is scanned by a plurality of angularly oriented scan planes 52. Since this is a top view of the volumetric regions, the scan planes 52 are viewed edge-on from the top. This drawing depicts the scanning of the volumetric region by nine scan planes spaced at uniform angular increments of rotation of 20°. These scan planes can be acquired by the scanhead 10 of FIG. 1 by rotating the array transducer 12 through 180° of rotation and acquiring a scan plane of image data at each increment of 20°. As FIG. 2 shows, when the axis of rotation is located at the center of the array transducer, the acquired scan planes of image data intersect at a common center point 54, the location of the axis of rotation. It is seen that there is a greater scan plane density at this center point of the volumetric region than exists at the periphery of the region where the angularly separated scan plane are more widely separated.

Figure 3:
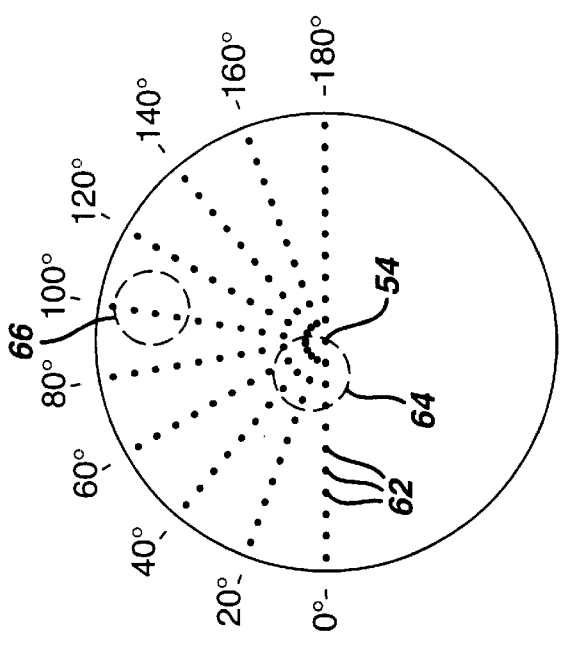
FIG. 3 illustrates the volumetric data density of a rotated scan plane with uniform beam spacing.

FIG. 3 depicts the locations of the beams or scanlines of each scan plane of FIG. 2 when the beams of each scan plane are uniformly spaced. In this example the beams are steered orthogonally to the surface of the array transducer such that the dots in FIG. 3 represent the view of each beam or scanline from its point of origin, looking into the volumetric region 50 from the top. For instance, there is a scan plane of twenty-one beams 62 extending between the 0° and 180° positions when the array transducer is in this position. The beams 62, viewed end-on, are uniformly spaced across the scan plane. It should be noted that a full scan plane is represented extending between the 0° and 180° positions, and only half of the other scan planes are shown above the 0° and 180° positions; a similar array of scan plane and beams is not shown but is also present in the lower half of the drawing.

Each beam is comprised of a sequence of samples acquired along the beam through the depth of the volumetric region. Since the beams are uniformly spaced along the scan plane, the volume is uniformly sampled within a given scan plane. However, when a plane orthogonal to the scan planes is examined such as that shown in FIG. 3, which is intersected by the beams of the numerous scan planes, the sampling effected by the beams is nonuniform. It is seen, for instance, that the dashed circle 64 drawn near the axis of rotation 54 is intersected and sampled by approximately fourteen beams, whereas the dashed circle 66 of the same size near the periphery of the volumetric region 50 is intersected and sampled by only about four beams. Thus, each plane orthogonal to the scan planes is more densely sampled in the center and more sparsely sampled at the periphery.

Figure 4B:
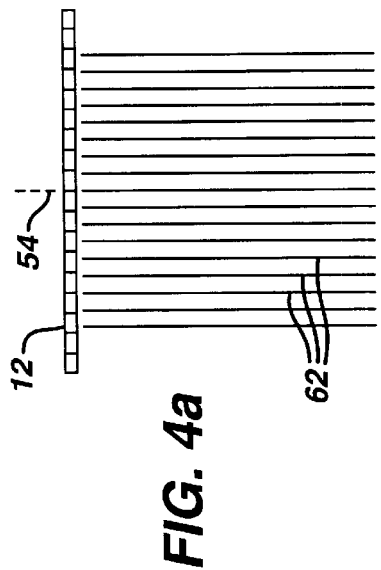
FIG. 4b illustrates a linear scan with nonuniformly spaced scanlines in accordance with the principle of the present invention.
Figure 4A:
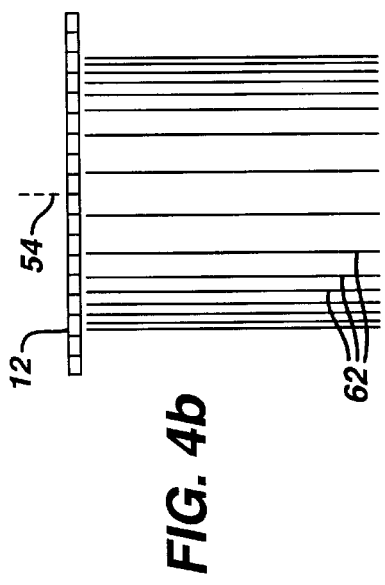
FIG. 4a illustrates a linear scan with uniformly spaced scanlines.

FIG. 4a illustrates a linear array scan of parallel steered, uniformly spaced beams 62 produced by an array transducer 12. An array transducer operated in this manner and rotated about a central axis 54 can be used to acquire the beams 62 shown in FIG. 3 with the result there illustrated. In accordance with the principles of the present invention, a more uniform spatial sampling is provided when the beams of the array transducer 12 are steered with a nonuniform distribution as shown in FIG. 4b. As this drawing illustrates, the beams are steered to be relatively widely spaced across the image plane in the vicinity of the central axis 54, and more densely spaced toward the ends of the array. The nonuniform planar beam density, when rotated to scan a volumetric region as shown in FIG. 2, will produce a more balanced sampling density between the center and the periphery of the volumetric region. At the periphery, where the scan planes are more widely separated due to their angular variation, the greater planar beam density will result in greater peripheral scanning density than in the case of FIG. 3. In the center of the volumetric region, where the scan planes are closer together, the sparser planar beam density will result in a decreased scanning density than in the case of FIG. 3. The spacing of the beams is preferably determined by the sampling criteria needed for the desired 3D image precision. The beams should be close enough together to adequately spatially sample the volumetric region so that the interpolation or filling in of spaces between scan planes will not result in aliasing or other artifacts caused by spatial undersampling. Preferably both the central and peripheral spatial sampling densities resulting from the spacing of beams within a scan plane and from the angular separation of the scan planes are chosen to be sufficient to satisfy the sampling criteria for adequate artifact-free spatial sampling.

Figure 5A:
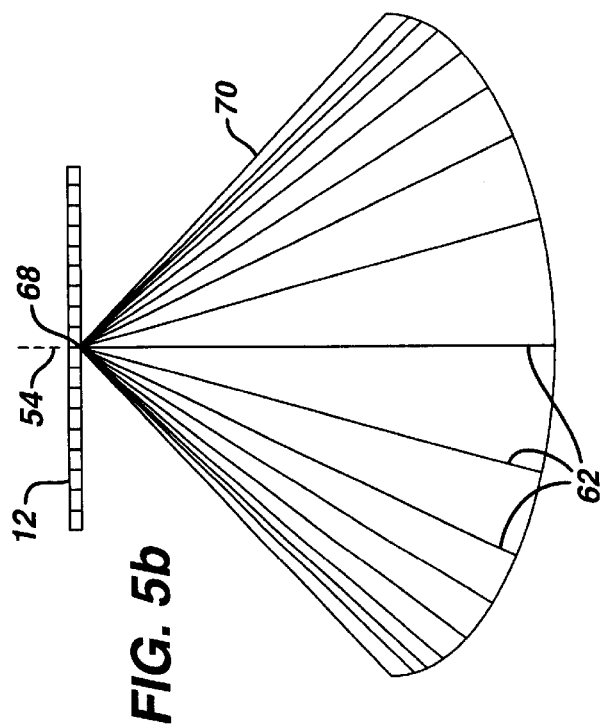
FIG. 5a illustrates a sector scan with uniformly spaced scanlines.
Figure 5B:
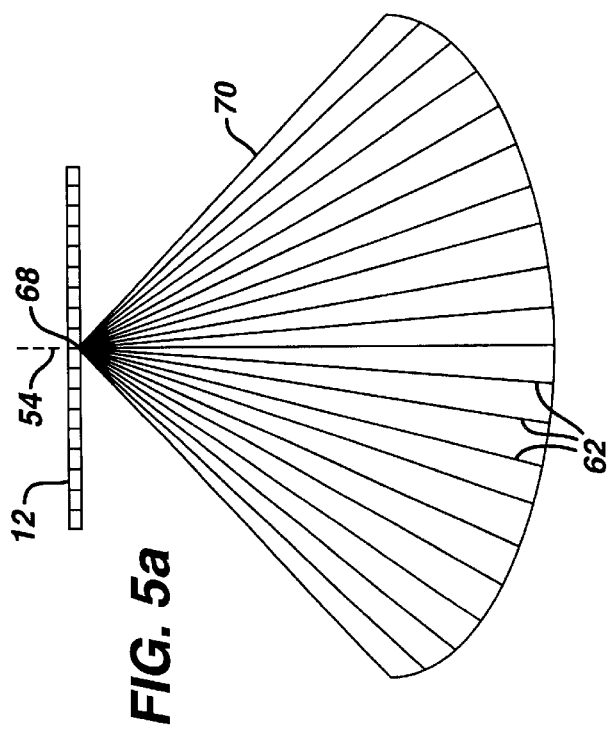
FIG. 5b illustrates a sector scan with nonuniformly spaced scanlines in accordance with the principle of the present invention.

FIG. 5a illustrates the operation of an array transducer 12 for phased array scanning by which the beams 62 are steered to emanate from a common origin or sector apex 68 to scan a sector 70. In various phased array embodiments the beams 62 may be steered to effectively emanate from a point behind the array transducer 12, called virtual apex scanning, or steered so that the apex is in front of the array transducer which, as mentioned in U.S. Pat. No. 5,487,388, is useful when imaging through the ribs of a patient. When the array transducer 12 is operated in this manner and rotated about a central axis 54, the beams 62 will scan a conical shaped volumetric region. As in the case of FIG. 3 the uniform beam spacing shown in FIG. 5*a* will result in a greater sampling density at the center of the conical shape than at the periphery, and a greater sampling density closer to the transducer array than at greater depths due to the varying angularity of the beams. The disparity of the sampling density between the center and the periphery of the conical shaped volume can be reduced in accordance with the principles of the present invention by steering the beams to have a greater separation at the center of the sector 70 than at the periphery, as shown in FIG. 5*b*. When the array transducer 12 is operated in this manner and rotated to sample a volumetric region at different angles of rotation, the disparity of the beam (sampling) density between the center and periphery of the volumetric region is reduced.

The principles of the present invention may also be applied to a two dimensional array transducer which allows beams to be electronically steered in both azimuth and elevation. For instance, the embodiment of FIG. 5*b* can comprise a 2D array transducer 12' in which the beams are steered electronically in azimuth and, instead of mechanically rotating the transducer, the beams are also electronically steered in elevation. The beams can all be steered to emanate from a common apex 68 and can be acquired in a planar sequence or in any other desired sequence due to the substitution of all electronic steering for electronic/mechanical steering. The steered beams will be more widely separated in the vicinity of the center of the volumetric region about a central axis 54, and more closely separated toward the periphery of the volumetric region to more evenly balance the sampling density between the interior and periphery of the volumetric region. Three dimensional images can be produced at a high rate of speed due to the elimination of the need to mechanically steer the beams in the elevation (rotational) direction.

What is claimed is:

1. A method for ultrasonically scanning a volumetric region by beams steered by an ultrasonic array transducer having elements which are uniformly paced in the azimuth dimension comprising the steps of:

steering the beams to be relatively more widely separated in the vicinity of the center of the volumetric region; and steering the beams to be relatively more closely separated in the vicinity of the periphery of the volumetric region, whereby the disparity in sampling density between the center and periphery of the volumetric region is reduced.

2. The method of claim 1, wherein the steps of steering further comprise electronically steering said beams in both azimuth and elevation.

3. The method of claim 1, wherein the steps of steering further comprise electronically steering said beams in azimuth, and further comprising the step of mechanically steering said beams in elevation.

4. The method of claim 3, wherein said step of mechanically steering said beams in elevation comprises rotating said array transducer about an axis of rotation, wherein said axis of rotation is in alignment with the center of the volumetric region being scanned.

5. The method of claim 4, wherein the steps of steering further comprise electronically steering beams in azimuth in an image plane to be relatively more widely separated at the center of the image plane than at the ends of the image plane.

6. The method of claim 5, wherein the steps of steering further comprise steering the beams of a linear array transducer.

7. The method of claim 5, wherein the steps of steering further comprise steering the beams of a phased array transducer.

8. An ultrasonic diagnostic imaging system which scans a volumetric region with steered beams in a relatively uniform manner comprising:

an array transducer having elements which are uniformly spaced in the azimuth dimension;

means, coupled to said array transducer, for electronically steering beams in azimuth to be relatively more widely separated toward the center of said volumetric region and relatively more closely separated toward the periphery of said volumetric region;

means, coupled to said means for electronically steering beams in azimuth for steering beams in elevation;

a 3D rendering processor coupled to receive signals produced by said array transducer for producing three dimensional display information; and a display device coupled to said 3D rendering processor for displaying a three dimensional ultrasonic image.

9. The ultrasonic diagnostic imaging system of claim 8, wherein said means for electronically steering beams in azimuth comprises a beamformer.

10. The ultrasonic diagnostic imaging system of claim 9, wherein said means for steering beams in elevation comprises means for rotating said array transducer.

11. The ultrasonic diagnostic imaging system of claim 10, wherein said array transducer comprises a linear array transducer; and wherein said beamformer steers beams in azimuth in an image plane.

12. The ultrasonic diagnostic imaging system of claim 10, wherein said array transducer comprises a phased array transducer; and wherein said beamformer steers beams in azimuth in an image plane.

13. The ultrasonic diagnostic imaging system of claim 9, wherein said array transducer comprises a 2D array transducer; and wherein said beamformer comprises means for electronically steering beams in both azimuth and elevation.

14. The ultrasonic diagnostic imaging system of claim 8, wherein said 3D rendering processor comprises a surface rendering processor.

15. The ultrasonic diagnostic imaging system of claim 8, wherein said 3D rendering processor comprises a volume rendering processor.

* * * * *